(12) United States Patent
Hajjar et al.

(10) Patent No.: US 12,064,120 B2
(45) Date of Patent: Aug. 20, 2024

(54) SYSTEMS AND METHODS FOR LEFT VENTRICULAR UNLOADING IN BIOLOGIC THERAPY OR VECTORED GENE THERAPY

(71) Applicant: ABIOMED, Inc., Danvers, MA (US)

(72) Inventors: Roger J Hajjar, Tenafly, NJ (US); Kiyotake Ishikawa, Fort Lee, NJ (US); Jerald Wayne Curran, Danvers, MA (US); Noam Josephy, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 765 days.

(21) Appl. No.: 16/832,924

(22) Filed: Mar. 27, 2020

(65) Prior Publication Data

US 2020/0305888 A1 Oct. 1, 2020

Related U.S. Application Data

(60) Provisional application No. 62/959,333, filed on Jan. 10, 2020, provisional application No. 62/826,444, filed on Mar. 29, 2019.

(51) Int. Cl.
*A61B 17/12* (2006.01)
*A61K 48/00* (2006.01)
(Continued)

(52) U.S. Cl.
CPC .. *A61B 17/12122* (2013.01); *A61B 17/12136* (2013.01); *A61K 48/005* (2013.01);
(Continued)

(58) Field of Classification Search
CPC ....... A61B 17/12122; A61B 17/12136; A61M 60/237; A61M 60/833; A61M 60/17;
(Continued)

(56) References Cited

U.S. PATENT DOCUMENTS 5,797,870 A * 8/1998 March ................ C07K 14/8125
604/28
6,152,141 A * 11/2000 Stevens ................ A61M 25/10
604/4.01

(Continued)

FOREIGN PATENT DOCUMENTS

| JP | H05161714 A | 6/1993 |
| JP | 2002136599 A | 5/2002 |
| JP | 2019502522 A | 1/2019 |

OTHER PUBLICATIONS

Wolfram, PHD., Julie A., "Gene Therapy to Treat Cardiovascular Disease", JAHA vol. 2, Issue 4 (2013) ("Wolfram").

(Continued)

*Primary Examiner* — Catherine M Voorhees
*Assistant Examiner* — Roland Dinga
(74) *Attorney, Agent, or Firm* — Botos Churchill IP Law LLP (57) ABSTRACT

Methods and systems for using mechanical circulatory support concurrently with a biologic therapy (e.g. a gene therapy vector). Particular adaptations include a cardiac therapy method in which a blood vessel such as a coronary artery or blood vessel is occluded, followed by injecting a gene therapy vector or biologic distal to the occlusion site and waiting a certain amount of time, while using the mechanical circulatory support system to provide circulatory support to the patient.

6 Claims, 7 Drawing Sheets

(51) Int. Cl.
  *A61M 60/17* (2021.01)
  *A61M 60/237* (2021.01)
  *A61M 60/833* (2021.01)
  *C12N 15/85* (2006.01)

(52) U.S. Cl.
  CPC .......... *A61K 48/0075* (2013.01); *A61M 60/17* (2021.01); *A61M 60/237* (2021.01); *A61M 60/833* (2021.01); *C12N 15/85* (2013.01); *A61M 2202/206* (2013.01)

(58) Field of Classification Search
  CPC ........... A61M 2202/206; A61K 48/005; A61K 48/0075; C12N 15/85
  See application file for complete search history.

(56) References Cited

U.S. PATENT DOCUMENTS

| | | | |
|---|---|---|---|
| 6,673,039 B1 | 1/2004 | Bridges et al. | |
| 6,800,068 B1* | 10/2004 | Dae | A61M 60/884 604/113 |
| 2004/0193107 A1* | 9/2004 | Pierpont | A61M 25/104 604/103.03 |
| 2006/0258980 A1* | 11/2006 | Bridges | A61M 25/1011 604/101.05 |
| 2009/0187144 A1* | 7/2009 | Jayaraman | A61M 25/1027 604/103.02 |
| 2013/0303830 A1 | 11/2013 | Zeng et al. | |
| 2017/0189654 A1 | 7/2017 | Schwartz et al. | |
| 2018/0360992 A1* | 12/2018 | Patel | C07K 14/475 |
| 2019/0216995 A1* | 7/2019 | Kapur | A61M 60/295 |

OTHER PUBLICATIONS

International Search Report and Written Opinion for Application No. PCT/US20/25307 dated Sep. 11, 2020.
Office Action from Indian Patent Application No. 202117047531 dated Oct. 9, 2023 (7 pp.).
Office Action from Japanese Patent Application No. 2021560405 dated Nov. 24, 2023 (6 pp.).
Office Action from corresponding Israeli Patent Application No. 286675 dated May 19, 2024 (4 pp.).

* cited by examiner

SYSTEMS AND METHODS FOR LEFT VENTRICULAR UNLOADING IN BIOLOGIC THERAPY OR VECTORED GENE THERAPY

CROSS-REFERENCE TO RELATED APPLICATIONS

This application claims priority of U.S. Provisional Application No. 62/826,444 filed Mar. 29, 2019 and U.S. Provisional Application No. 62/959,333, filed Jan. 10, 2020, both of which are incorporated by reference herein.

BACKGROUND

Cardiovascular diseases are a leading cause of morbidity, mortality, and burden on healthcare around the world. A variety of treatment modalities have been developed for cardiovascular disease, ranging from pharmaceuticals to mechanical devices and finally transplantation. Temporary cardiac support devices, such as ventricular assist devices, provide hemodynamic support, and facilitate heart recovery. Some ventricular assist devices are percutaneously inserted into the heart and can run in parallel with the native heart to supplement cardiac output, such as the IMPELLA® family of devices (Abiomed, Inc., Danvers MA).

Genetic manipulation through the transfer of genes to a target can be used to treat cells or organs, such as the heart. See e.g. Julie A. Wolfram, PhD et al., *Gene Therapy to Treat Cardiovascular Disease*, JAHA Vol 2, Issue 4 (2013) ("Wolfram"), incorporated herein by reference in its entirety. Gene therapy methods include the use of one or more gene therapy vectors, either viral or non-viral. For viral vectors, the genome of a virus can be programmed, and the virus injected into a patient as a gene therapy vector, with the expectation that the virus genome will express in the patient. At least one example of viral vectors includes adeno-associated viruses (AAVs). Administration of the vector can be done through injections or perfusions in different locations. For example, coronary perfusion can be used to deliver a vector genome globally across the myocardium. High gene expression is generally needed to achieve a therapeutic effect. At least one disadvantage of administering the viral vector in a coronary is the relative inefficiency of the technique, as the vector genome is rapidly delivered into system circulation by the heart. Due to the heart pumping, the clearance rate of the vector genome through the heart can be too high to achieve the desired gene expression. The virus passes through the heart relatively quickly, with relatively little time to adhere to the myocardium and transduce enough of the myocardium. The same issues arise with administration of biologic therapies to the heart. Techniques which arrest the heart to reduce the clearance rate of the vector genome or biologic and increase retention in the heart result in cardiac instability and/or ischemia.

It is therefore desirable to have systems and methods which can reduce the clearance rate of a vector genome or biologic in the heart without the downsides associated with stopping or slowing the heart.

BRIEF SUMMARY

The methods, systems, and devices described herein enable efficient delivery of biologic therapy, such as, but not limited to, a gene therapy vector to the myocardium by (i) temporarily blocking blood flow to the myocardium to increase the uptake of the biologic therapy (e.g. a gene therapy vector) in the myocardium and reduce clearance of the biologic therapy (e.g. the gene therapy vector) through the heart 110, (ii) while operating a mechanical circulatory support device 120 in the heart 110 concurrently with the injection of the biologic therapy (e.g. vector gene therapy) to maintain heart function and systemic circulation without adverse effects for the patient 140. At least one advantage of these methods, systems and devices is the ability to increase deposition of the biologic therapy (e.g. the gene therapy vector) within the myocardium. By deploying an angioplasty balloon 130 in at least one coronary (i.e. the arteries and vessels with surround and supply the heart 110) to temporarily stop blood flow, and injecting a biologic therapy such as a gene therapy vector virus distal of the deployed balloon 130, the virus medium is pooled in the coronary artery, providing the therapy such as the virus vector with significantly more time to transduce the heart muscle. Operating a mechanical circulatory support device 120 while injecting the biologic therapy maintains the cardiac output necessary for life and bridges the patient through potential ischemic events caused by the inflated angioplasty balloon 130—the mechanical circulatory support device 120 acting as a temporary heart bypass. The mechanical support device 120 can be a blood pump 120, such as an Impella device. In some embodiments, biologic therapy such as a gene therapy vector can be targeted to particular heart tissues, such as fibroblasts or endothelial cells. In some embodiments, one or more gene therapy vectors can be employed to preferentially target myocytes, fibroblasts, endothelial cells or other target tissues.

In a first illustrative embodiment, a method of treating a heart 110 comprises operating a mechanical circulatory support device 120 to support the heart 110. In some embodiments, the mechanical circulatory support device 120 is operated outside the patient 140 and in other embodiments the mechanical circulatory support device 120 is inserted into the patient 140. The method further comprises operating the mechanical circulatory support device 120 for a support period, and administering a biologic therapy such as a gene therapy vector to the heart 110 during the support period. In an example, the gene therapy vector is administered within a blood vessel in the heart 110. In another example, the method further comprises inserting an angioplasty balloon 130 in the blood vessel and inflating the balloon 130 to temporarily occlude the blood vessel. In one example, the gene therapy vector is administered to the heart 110 at a location distal of the angioplasty balloon 130. For example, the gene therapy vector is administered within the coronary artery downstream from the inflated balloon 130. In some examples, the gene therapy vector can be administered over the course of several periods. For example, a first dose of gene therapy vector is administered to the heart 110 during a first administration period, followed by a second dose of gene therapy vector to the heart 110 during a second administration period, with both administration periods separated by a rest period. In one example the rest period is longer than the first administration period. In one example, the inflated angioplasty balloon 130 temporarily occludes the vessel for less than about three minutes, preferably one minute. In one example, the support period during which the mechanical circulatory support device 120, e.g. a microaxial transvalvular pump, is used is longer than 10 minutes. The support device is operated during the different administration periods and the rest period. In an example, administering the gene therapy vector to the heart 110 is configured to increase an expression of vector DNA in cardiac tissue. The gene therapy vector may be targeted to tissues within the heart 110 including the myocardium, fibroblasts, endothelial cells, or other cardiac tissue.

In a second illustrative embodiment, a method of supporting a patient's heart 110, comprises percutaneously inserting a blood pump 120 into the heart 110 and positioning the blood pump 120 across the aortic valve of the heart 110. The method further comprises operating the blood pump 120 to unload the left ventricle of the heart 110, and concurrently operating the blood pump 120 and injecting a gene therapy vector into a coronary of the heart 110 that is occluded in the manner described herein.

In a third illustrative embodiment, a method of upregulating gene expression in a patient's myocardium comprises placing a balloon 130 in a coronary artery of a patient 140, and inflating the balloon 130 for a first period to temporarily block blood flow within the coronary artery during the first period. The method further comprises placing a blood pump 120 into a heart 110 of the patient and positioning the pump across an aortic valve of the heart 110 before operating the blood pump 120 in the heart of the patient during a second period. The method comprises injecting a gene therapy vector within the coronary artery at a location distal of the inflated balloon 130 during the first period, and deflating the balloon 130 after the first period to restore blood flow within the coronary artery. In this illustrative embodiment, the first period occurs during the second period and the first period has a duration that does not cause permanent ischemia in cells of the myocardium. In one example, the method includes injecting the biologic therapy such as the gene therapy vector within the coronary artery at the location distal of the inflated balloon 130 during the second period. In another example, the method includes injecting the gene therapy vector within the coronary artery at the location distal of the inflated balloon 130 during a third period less than or equal to the second period. The duration of the first period may be less than three minutes, preferably less than one minute.

In a fourth illustrative embodiment, a method of supporting a patient's heart 110 comprises administering biologic therapy such as a gene therapy vector within the heart 110. The method further comprises reducing the rate of clearance of the biologic therapy such as the gene therapy vector through the heart 110. In those embodiments where the biologic therapy is a gene therapy vector, the reduced rate of clearance causes expression of the gene therapy vector in the heart 110, causing transduction of the heart 110 by the gene therapy vector, or any combination of these. In one example, the method deploys a mechanical circulatory support device 120 and a balloon catheter to the heart 110.

In a fifth illustrative embodiment, a cardioprotective system 100 for supporting a patient's heart 110 that has undergone cardiogenic shock or myocardial infarction deploys a mechanical circulatory support device 120 configured to be inserted and operated in the patient 140 and a balloon catheter having an inflatable balloon 130 with a proximal end and a distal end. The balloon catheter comprises an inflation catheter in fluid connection with the proximal end of the balloon 130, and the balloon 130 configured to be inserted in a coronary artery of the patient 140 for concurrent use with the mechanical circulatory support device 120. The system further deploys a delivery catheter for delivering a gene vector therapy in vivo, the delivery catheter having a proximal end with an inlet opening configured to receive a solution containing the gene therapy vector, a distal end with an outlet opening, and a tube extending between the proximal and distal ends of the delivery catheter. The balloon 130 is configured to occlude blood flow at least partially through the coronary artery when inflated. In one example, the mechanical circulatory support device 120 is a catheter-based intravascular blood pump. In another example, the outlet opening is configured to be positioned distal of the distal end of the balloon 130 when the balloon 130 is inflated. In yet another example, the tube extending between the proximal and distal ends of the delivery catheter has a longitudinal length that is longer than the balloon 130. In another example, the balloon catheter is configured such that upon balloon 130 inflation, the balloon catheter outlet opening is not impeded by the balloon 130. In those embodiments where the gene therapy vector is administered, the vector may Include non-native nucleic acid material that codes for a peptide that has a cardioprotective function when expressed in vivo, the gene therapy vector being configured to be absorbed by myocardial cells.

In a sixth illustrative embodiment, a method of treating a heart 110 includes operating a mechanical circulatory support device 120 to support the heart 110. The method further includes operating the mechanical circulatory support device 120 for a support period, occluding at least one heart vessel and administering a biologic therapy to the occluded heart vessel. Biologic therapies can be adapted to preferentially target myocytes, fibroblasts, endothelial cells or other target tissues.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems and methods described herein, certain illustrative implementations will be described. Although the implementations and features described herein are specifically described for use in connection with a circulatory and reperfusion therapy system, it will be understood that all the components and other features outlined below may be combined with one another in any suitable manner and may be adapted and applied to other types of circulatory therapy and reperfusion therapy devices.

As noted above, in one embodiment a gene therapy vector is introduced into an occluded vessel of a mechanically supported heart. FIGS. 1-6 illustrate results obtained in a gene therapy vector study performed on pigs. For a first control group of pigs. Pigs in the study were numbered—pig 5 being referred to as IGT5, pig 6 being referred to as IGT6, etc. Three groups of pigs were considered. In a first control group of pigs ("Group 1"), an adeno-associated virus type 6 vector (AAV6) with Luciferase (an enzyme producing bioluminescence) was injected into a coronary—no angioplasty balloon or mechanical circulatory system device was used. In a second group of pigs ("Group 2"), the left ventricle was unloaded with a mechanical circulatory system device (an Impella pump) while the gene therapy vector was injected into the coronary—no angioplasty balloon was used. In a third group of pigs ("Group 3"), an angioplasty balloon was deployed in the coronary, the gene therapy vector was injected into the coronary distal of the balloon, and a mechanical circulatory system device (an Impella pump) was used concurrently with the injection. As part of the study protocol, gene therapy vector injection was performed in phases—with a first injection phase followed by a period with no injection, then a second injection phase followed by a period with no injection, and finally a third injection phase followed by a period with no injection.

Figure 1:
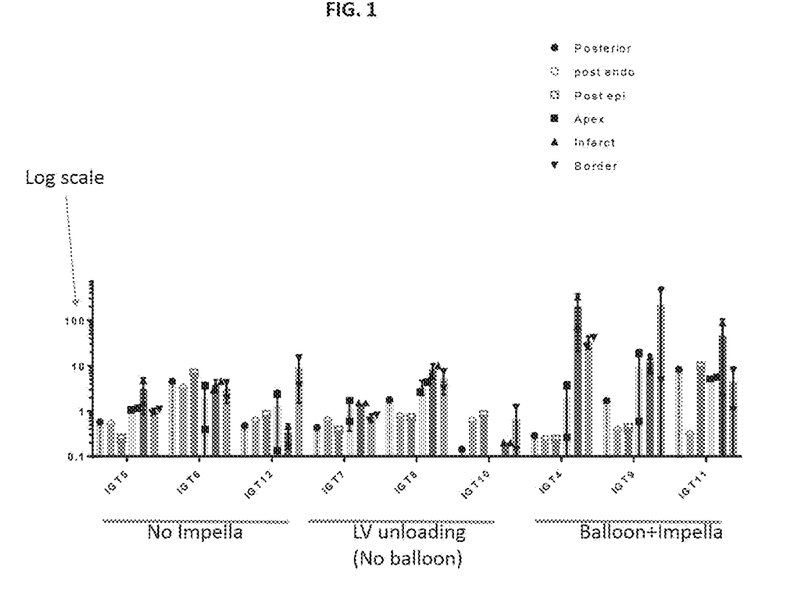
FIG. 1 illustrates levels of gene expression in different heart tissues for three groups of pigs having undergone biologic therapy using a viral gene therapy vector (i) without Impella support (pigs IGT5, IGT6, IGT12), (ii) with Impella support but without an angioplasty balloon (pigs IGT7, IGT8, IGT10), and (iii) with Impella support combined with an angioplasty balloon (pigs IGT4, IGT9, IGT11)

FIG. 1 illustrates results obtained during the pig study for the three groups of pigs. The Y axis measures Luciferase levels in tissue biopsies, with Luciferase levels being correlated to a number of genes expressed in the myocyte. If Luciferase is expressed, the assay glows, and the intensity of the glow is correlated to the amount of vector genome expressed in the tissue. The Y-axis uses a logarithmic scale, with a value of 1 indicating standard genome expression. The various data points (posterior, post endo, post epi, Apex, infarct, border) correspond to different regions of the heart muscle in which biopsies were taken. As shown in FIG. 1, compared to Group 1 (No Impella), and Group 2 (Impella but no balloon), the pigs in Group 3 (Balloon and Impella) show levels of vector genome expression which are logarithmically higher than the levels of vector genome expression for Group 1 or Group 2. At least one advantage of the concurrent use of the angioplasty balloon and the mechanical circulatory support device is the ability to prolong the time that the gene therapy vector medium is pooled in the myocardium, while maintaining cardiac stability. Deployment of the angioplasty balloon is relatively short, e.g. less than one (1) minute—occlusion of the coronary may result in some myocardial stunning (brief moments of tissue ischemia) but the effects of myocardial stunning are reversible.

Figure 2:
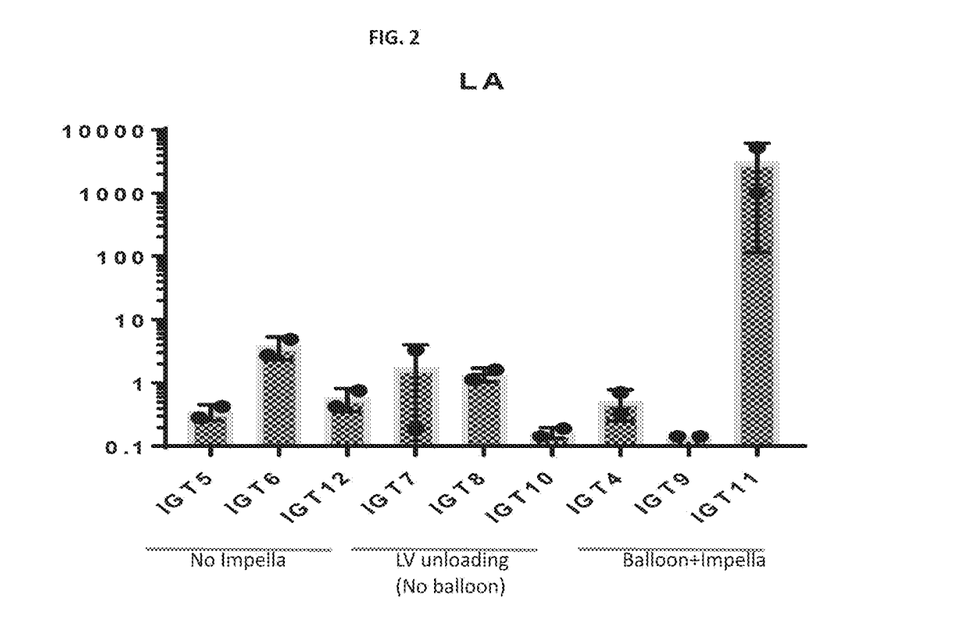
FIG. 2 illustrates levels of gene expression in left atrial tissue for the three groups of pigs of FIG. 1—the pigs having undergone biologic therapy using a viral gene therapy vector (i) without Impella support (pigs IGT5, IGT6, IGT12), (ii) with Impella support but without an angioplasty balloon (pigs IGT7, IGT8, IGT10), and (iii) with Impella support combined with an angioplasty balloon (pigs IGT4, IGT9, IGT11)

FIG. 2 illustrates levels of vector genome expression, in a format similar to FIG. 1, but for left atrial tissue biopsies. As shown in FIG. 2, of Group 3, one pig—Pig 11 (IGT11)—had a 3000 fold increase in luciferase activity, indicating extremely high level of gene expression.

Figure 3:
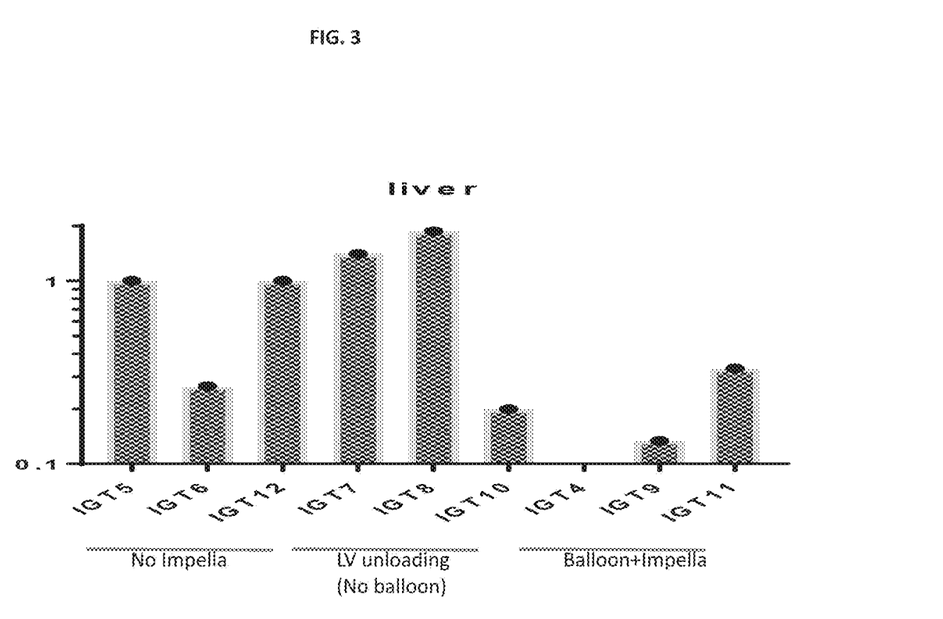
FIG. 3 illustrates levels of gene expression in liver tissue for the three groups of pigs of FIG. 1—the pigs having undergone biologic therapy using a viral gene therapy vector (i) without Impella support (pigs IGT5, IGT6, IGT12), (ii) with Impella support but without an angioplasty balloon (pigs IGT7, IGT8, IGT10), and (iii) with Impella support combined with an angioplasty balloon (pigs IGT4, IGT9, IGT11)

FIG. 3 illustrates levels of vector genome expression in a format similar to FIG. 1, but for liver tissue biopsies. When using a biologic therapy that deploys a virus vector, minimizing a presence of the virus outside of the target organ is desirable. Preferably, levels of the virus in a patient's systemic circulation should be low. Organs such as the liver, which are intended to clear systemic circulation indicate an extent to which the virus was evacuated from the system prior to reaching the liver. As shown in FIG. 3, for pigs of Group 3, levels of expression in the liver are lower than the expected expression value of 1. This indicates that most of the vector virus is output near the injection site—i.e. into the heart muscle, with only desirably low amounts of the vector virus reaching the liver.

Figure 4:
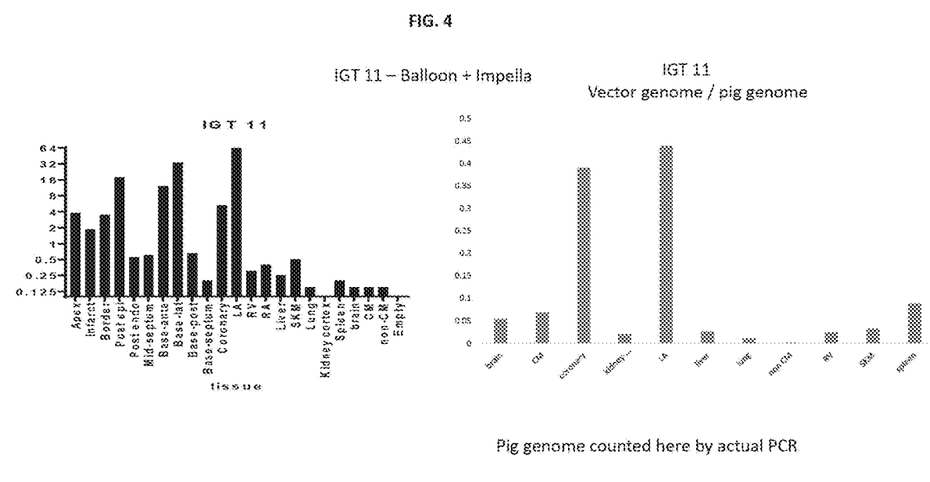
FIG. 4 illustrates vector genome expression for one pig (pig IGT11) having undergone biologic therapy using a viral gene therapy vector with Impella support and an angioplasty balloon, using PCR to count the vector genome and pig genome.

FIG. 4 illustrates levels of vector genome expression for pig 11 of the same pig study but in a different format than FIGS. 1-3. FIG. 4 shows results of a biologic therapy that deploys a gene therapy vector using a PCR test—a polymerase chain reaction test. The results of the therapy that deployed a gene therapy vector for pig 11 (part of Group 3: Impella and angioplasty balloon use) using PCR are consistent with the results shown in FIGS. 1-3: pig 11 (and pigs of group 3) exhibits significantly higher levels of vector gene expression in certain heart tissues than in the rest of its system. In the left-hand side graph, the y-axis measures gene expression via PCR, and the x-axis corresponds to different biopsies from different tissue areas. PCR levels are much higher for tissue areas corresponding to the heart (Apex, Infarct, Border, Post epi, Post endo, Mid-septum, Base-ante, Base-lat, Base-post, Base-septum, coronary and left atrium) than they are for other tissue areas (RV, RA, Liver, SKM, Lung, Kidney cortex, spleen, brain, CM, non-CM). This confirms that the vast majority of the gene therapy vector is being expressed in the heart tissue, and other organs have very low expression. Similarly, in the right-hand side graph, a ratio of vector genome normalized by the pig genome for pig 11 (IGT11) is significantly higher in the coronary and left atrium tissue biopsies than it is in any other tissue biopsy (brain, CM, kidney, liver, lung, non CM, RV, SKI, spleen).

Figure 5:
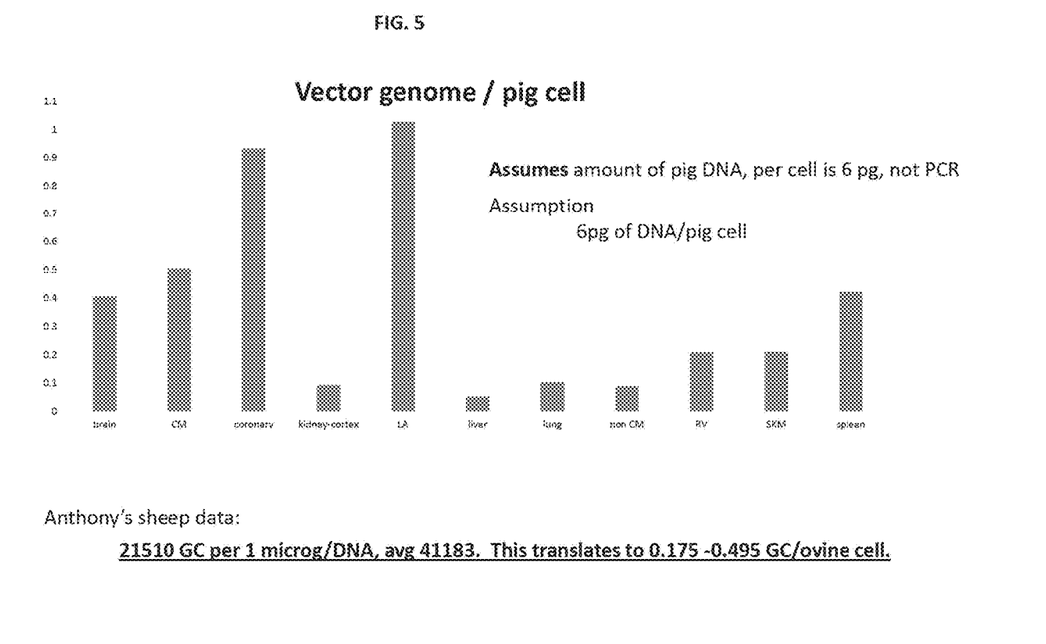
FIG. 5 illustrates vector genome expression for one pig (pig IGT11) having undergone biologic therapy using a viral gene therapy vector with Impella support and an angioplasty balloon, assuming a certain weight of DNA per pig cell.

FIG. 5 displays another indicator of the gene therapy vector expression for the pig study. The therapy vector genome is normalized by the amount of DNA in a pig cell, assuming there are 6 pg of DNA/pig cell. Again, ratios of therapy vector genome to pig genome are highest in the left atrium and coronary tissue biopsies, indicating that the left atrium and coronary are where the gene therapy vector is most efficient.

Figure 6:
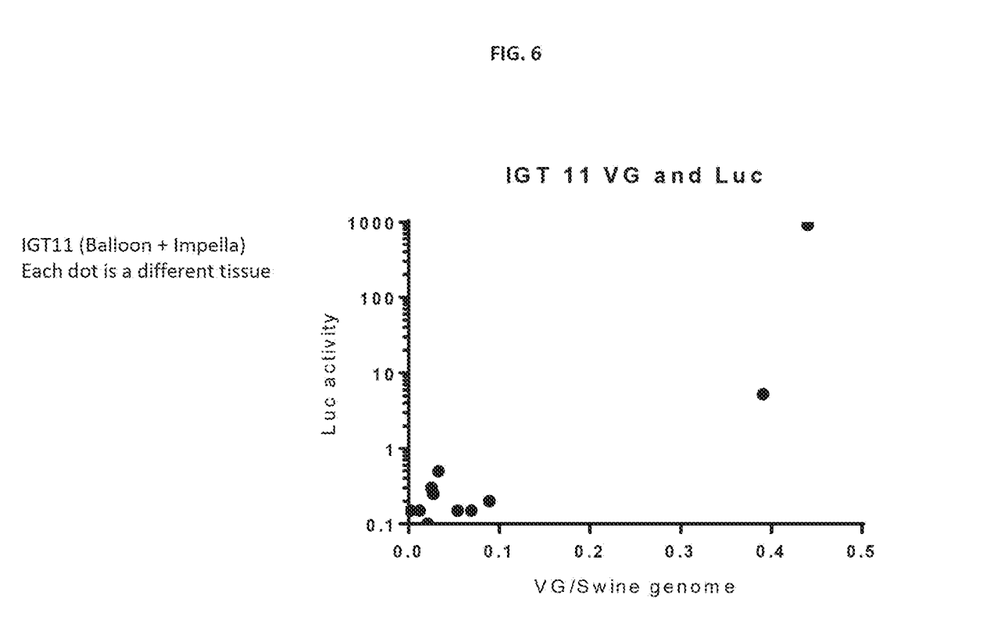
FIG. 6 illustrates for different tissue samples a correlation between luciferase activity and vector genome expression for one pig (pig IGT11) having undergone biologic therapy using a gene therapy vector with Impella support and an angioplasty balloon.
Figure 7:
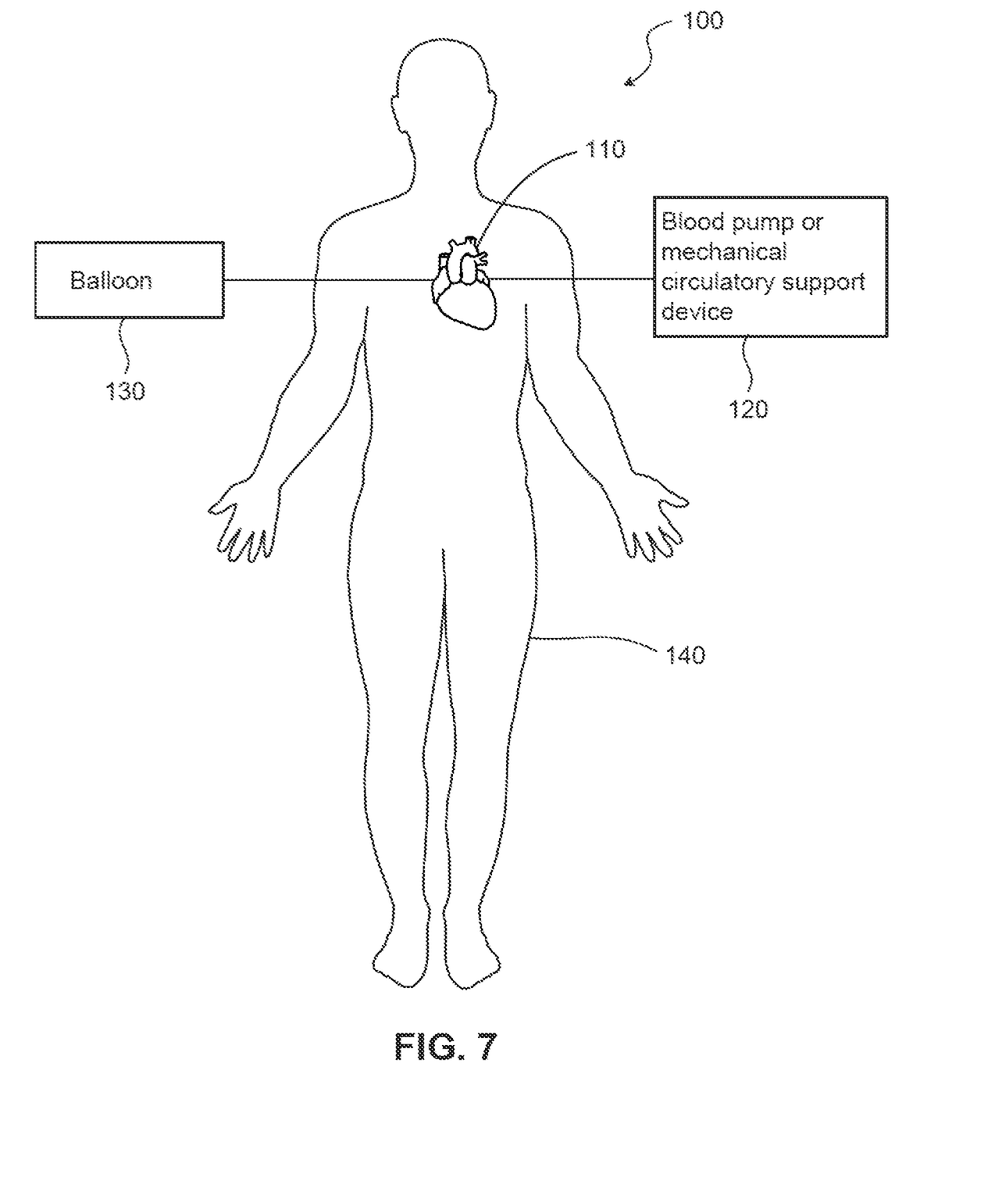
FIG. 7 illustrates a cardioprotective system with a mechanical support device or a blood pump and a balloon according an exemplary embodiment of the present disclosure.

FIG. 6 illustrates a correlation between both types of gene therapy vector indicators considered in FIGS. 1-3 (Luciferase) and in FIGS. 4-5 (PCR). FIG. 6 maps luciferase activity on the y-axis and a ratio of vector genome/swine genome on the x-axis. FIG. 6 confirms that luciferase activity is directly related to viral genome (VG) expression. The higher the ratio of vector genome to swine genome, the higher the luciferase (Luc) activity.

The same technique described above with regard to a gene therapy vector may be used to increase uptake of other biologics including stem cells, RNA, mRNA, antisense oligonucleotide therapies, polypeptides, or any other biologic for intake in the heart. For example, the method can be used with oligonucleotides to interfere with gene production in the heart, or any other molecule with similar function. In another example, biologics targeted to manage or inhibit the inflammatory response of cardiac tissue may be injected into the heart, such as proprotein convertase subtilisin kexin type 9 (PCSK9), tumor necrosis factor (TNF) inhibitor, or RNA interference biologics. The treatment of heart disease and cardiac symptoms can be improved through intracoronary injection of various biologics to the myocardium or any other targets tissues type such as fibroblasts or endothelial cells. Biologic therapies can be adapted to preferentially target myocytes, fibroblasts, endothelial cells or other target tissues.

The biologic therapy is administered within a blood vessel in the heart, and may be administered in combination with the use of an angioplasty balloon in the blood vessel to temporarily occlude the vessel. The biologic therapy may be administered at a location in the heart distal of the angioplasty balloon, for example in the coronary artery distal of the angioplasty balloon. In some examples, the biologic therapy is administered over the course of several periods, interspersed with rest periods during which the biologic therapy is not administered. The rest period may be longer than the periods of administration of the biologic therapy.

Biologics can be injected into the heart in combination with each other or in combination with gene vector therapies, as indicated by the cardiac symptoms. For the delivery of any biologic to the myocardium or any other targeted tissues type such as fibroblasts or endothelial cells, the blood flow within a vessel is temporarily blocked to increase uptake of the biologic in the cardiac tissue and reduce clearance of the biologic through the heart while concurrently operating a mechanical circulatory support device in the heart to maintain heart function and systemic circulation without adverse effect to the patient. By blocking the blood flow during administration of the biologic, the biologic has more time in contact with the cardiac tissue to transduce the desired tissue target.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. For example, whilst the disclosure has described the detection of movements such as hand/arm based gestures and roll-overs, the same principal is applicable to other large scale motions, such as user moving between a lying and a sitting position in bed (and vice versa), reaching for a specific target (a table lamp, or a respiratory apparatus) etc.

It will further be understood that any reference herein to subject matter known in the field does not, unless the contrary indication appears, constitute an admission that such subject matter is commonly known by those skilled in the art to which the present technology relates.

The invention claimed is:

1. A method of upregulating gene expression in a patient's myocardium, comprising the steps of:
   placing a balloon in a coronary artery of a patient;
   inflating the balloon for a first period to temporarily block blood flow within the coronary artery during the first period;
   placing a blood pump into a heart of the patient and positioning the blood pump across an aortic valve of the heart;
   operating the blood pump in the heart of the patient during a second period; and
   during the first period, injecting a gene therapy vector within the coronary artery at a location distal of the inflated balloon, and
   deflating the inflated balloon after the first period to restore blood flow within the coronary artery, wherein the first period occurs during the second period and the first period has a duration that does not cause permanent ischemia in cells of the patient's myocardium.

2. The method of claim 1, further comprising:
   during the second period, injecting the gene therapy vector within the coronary artery at the location distal of the inflated balloon.

3. The method of claim 2, further comprising:
   during a third period, injecting the gene therapy vector within the coronary artery at the location distal of the inflated balloon, wherein the third period is less than or equal to the second period.

4. The method of claim 1, wherein the duration of the first period is less than three minutes.

5. The method of claim 4, wherein the duration of the first period is less than one minute.

6. The method of claim 5, wherein the duration of the first period is less than thirty seconds.

* * * * *